United States Patent [19]

Booth, Jr. et al.

[11] Patent Number: 4,869,407
[45] Date of Patent: Sep. 26, 1989

[54] AIR-FRESHENER APPARATUS

[75] Inventors: Alfred E. Booth, Jr.; Robert L. Booth, both of Torrance, Calif.

[73] Assignee: Products by DesignAir, Inc., Marina del Ray, Calif.

[21] Appl. No.: 182,129

[22] Filed: Apr. 15, 1988

[51] Int. Cl.⁴ .............................................. A61L 9/12
[52] U.S. Cl. .................................. 222/633; 206/461; 206/471; 239/326; 239/327; 422/124
[58] Field of Search .................. 222/632, 633; 239/36, 239/53–57, 60, 145, 326, 327; 422/123, 124; 206/461, 471

[56] References Cited

U.S. PATENT DOCUMENTS

| | | | |
|---|---|---|---|
| 3,891,088 | 6/1975 | Huebner | 206/461 |
| 4,146,566 | 3/1979 | Gaiser | 422/123 |
| 4,208,012 | 6/1980 | Dutcher | 239/57 |
| 4,283,011 | 8/1981 | Spector | 239/57 |
| 4,306,679 | 12/1981 | Dusek et al. | 239/59 |
| 4,327,056 | 4/1982 | Gaiser | 239/57 |
| 4,523,870 | 6/1985 | Spector | 239/57 |

FOREIGN PATENT DOCUMENTS 1127487 9/1968 United Kingdom ............... 206/461

Primary Examiner—Andres Kashnikow
Assistant Examiner—Karen B. Merritt
Attorney, Agent, or Firm—Kenneth R. Glaser

[57] ABSTRACT

Air freshener apparatus comprising a cup-like base in which a quantity of fragrance emitting ingredient is disposed in at least a partially exposed relation. Secured air sealed about the support is a tubular bellows a soft, pliable composition forming an air chamber overlying the exposed relation of the fragrance ingredient. Breather holes formed through the support underlying the fragrance ingredient therein enables dispensing of a controlled quantity of fragrance scent by manually compressing the bellows. An adhesive pad on the undersurface of the support enables the apparatus to be attached to a recipient surface. Merchandise packaging of an air freshener unit includes a blister wrap of pliable composition having an aperture communicating from inward to outward thereof. This enables on-site consumer testing of the unit by depressing the wrap which in turn compresses the bellows to effect a scent emission outward through said aperture.

11 Claims, 2 Drawing Sheets

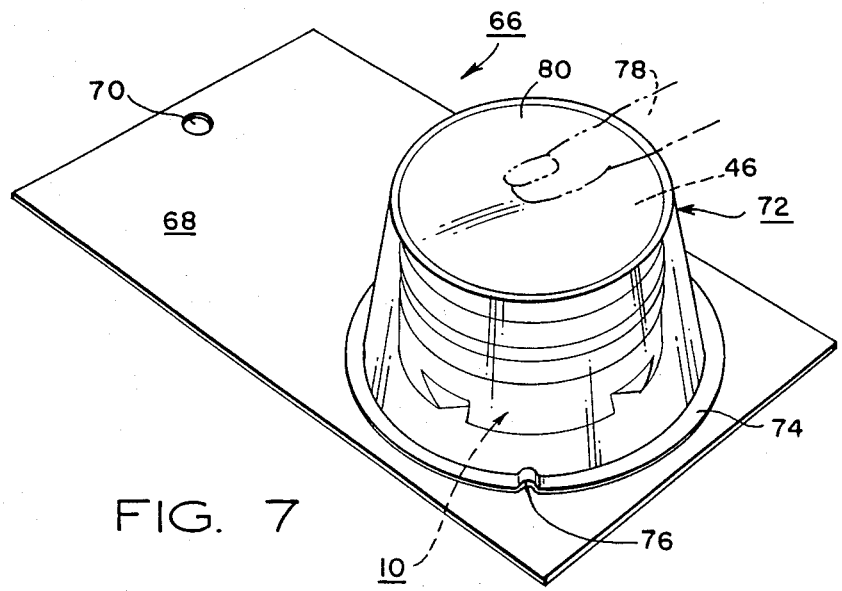
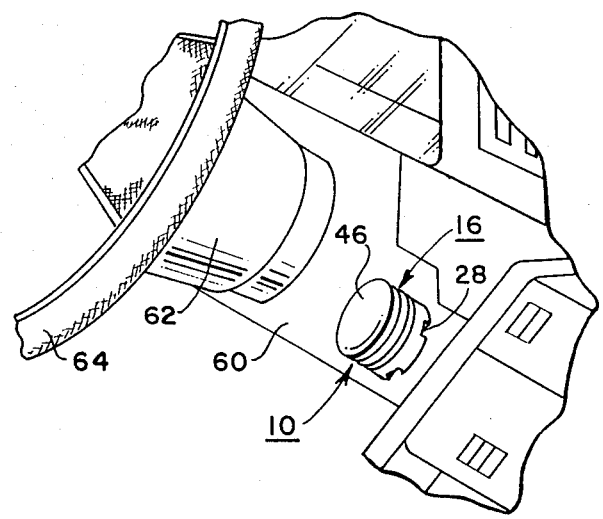

AIR-FRESHENER APPARATUS

TECHNICAL FIELD

The field of art to which the invention pertains comprises the art of air freshener apparatus by which a fragrance scent is dispensed to a surrounding air space.

BACKGROUND OF THE INVENTION

Air fresheners are a widely used commodity wherever odors are present and there is a conscious need to "freshen" the surrounding air. Typical applications for the air freshener are in a kitchen, restroom or automobile where there is a propensity for odors to accumulate and linger. The effect of the air freshener is to emit a selected fragrance scent that serves to dispel or neutralize the offensive effects of the odors which are otherwise present to at least enhance the apparent quality of air thereabout. Typically, the air freshener composition is in a liquid, powder or gel form from which the scent is dispensed by various means such as an exposed air wick, gravity air circulation through an open cannister, a manually actuated aerosol, etc., as are well known in the art.

BACKGROUND OF THE PRIOR ART

Air freshener apparatus of the prior art is available in a variety of forms depending on the composition format of the fragrance composition and the specific application for which it is to be used. In areas in which odors are being continuously generated or where the odors tend to linger for long periods of time, it is common to use an evaporative gel in a cannister exposing the gel to ambient air circulation. Also useful in that application is a liquid fragrance composition utilizing an air exposed wick applicator from which the liquid fragrance evaporates to the ambient air. For use in automobiles, it is common to employ a button or dish size capsule that can be conveniently placed in an obscure location about the auto interior such as on the dashboard. Via an opening of the container whether fixed or adjustable, the freshening ingredient is exposed to air for continuous emission of a fragrance scent until the supply of th operative fragrance ingredient is dissipated.

For more occasional or spontaneous needs, the aerosol can is frequently preferred by which large amounts of atomized air freshener ingredient can be quickly and widely dispensed on demand.

OBJECTS OF THE INVENTION

It is therefore an object of the invention to provide a novel air freshener apparatus for dispensing a fragrance scent to a surrounding air space.

It is a further object of the invention to effect the previous object with an air freshener apparatus that is effective to dispense controlled quantities of air freshener fragrance only on demand.

It is a still further object of the invention to effect the previous objects with an apparatus that is of relatively compact size, can be surface mounted, and is manually demand operative for a forced air dispensing of air freshener ingredient in controlled quantities.

SUMMARY OF THE INVENTION

This invention relates to air freshener apparatus for enhancing apparent air quality as well as a unique merchandise package therefor. More specifically, the air freshener apparatus of the invention hereof relates to novel apparatus manually actuated for dispensing a fragrance ingredient to a surrounding air space on demand.

The foregoing is achieved in accordance herewith by means of an air freshener fragrance dispenser comprised of a relatively small annular cup-like base of substantially rigid composition. The base defines an internal shelf on which is supported a fragrance source, such as a rigid fragrance wafer, overlying an open cavity formed by a generally closed wall of the base bottom. Radial recessed indentations about the exterior of the cavity each include a breather hole through which controlled quantities of fragrance scent can be emitted when the unit is manually actuated. The fragrance wafer is of a commercially available type and may be of a rigid and porous paper base pad which has been previously impregnated with oils of the particular fragrance. The top of the cup-like base is open so as to expose the upper surface of the wafer to an internal air chamber formed by a surrounding resilient tubular bellows assembly secured in an air sealed manner to the base.

The bellows is soft and pliable and easily finger depressed. Depressing the bellows thus tends to force a controlled quantity of air flow from the internal chamber past and through the wafer to be emitted outward through the breather holes to the surrounding air space. Therefore, when the bellows is compressed by finger depression applied thereto, a controlled quantity of the fragrance scent is emitted on demand. The bellows is so constructed to readily revert to its original shape upon release of finger depression; thus, the bellows can be operated repeatedly until a desired fragrance level in the surrounding air space is achieved. Mounted on the underside of the base is an adhesive patch by which the entire unit can be permanently secured to any desired surface where it is conveniently accessible and readily operated when required.

In accordance with a particular and additional feature, the air freshener fragrance dispenser of the invention is disposed in a uniquely designed merchandise display package which enables a prospective purchaser to activate the dispenser and sample the fragrance aroma without destroying or opening the package.

The above-noted features and advantages of the invention as well as other superior aspects thereof will be further appreciated by those skilled in the art upon reading the detailed description which follows in conjunction with the drawings.

BRIEF DESCRIPTION OF THE DRAWINGS

FIG. 6 is a fragmentary isometric view of the apparatus mounted on the dashboard of an automobile; and FIG. 7 is an isometric view of the air freshener apparatus hereof in its unique on-sale packaging for merchandising the product.

DESCRIPTION OF THE PREFERRED EMBODIMENT

Figure 1:
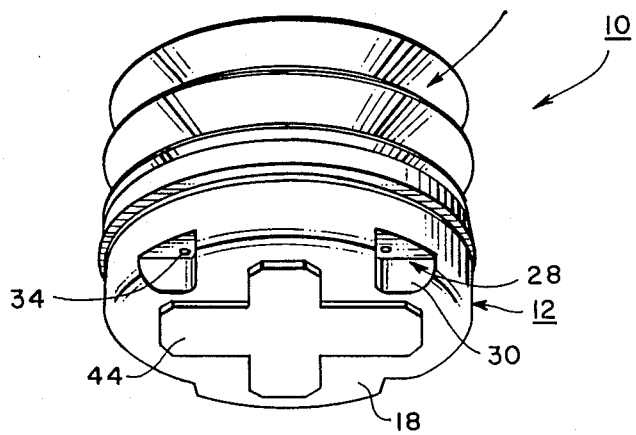
FIG. 1 is bottom side perspective view of the air freshener apparatus hereof.

In the description which follows, like parts are marked throughout the specification and drawings with the same reference numerals respectively. The drawing figures are not necessarily to scale and the proportions of certain parts may have been exaggerated for purposes of clarity.

Referring now to the drawings, the air freshener fragrance dispenser apparatus hereof is designated 10 and is comprised of a relatively rigid cup-like base receptacle 12 (containing the fragrance source material 14) in combination with a soft resilient elongated tubular bellows 16 coaxially mounted on the base.

Figure 5:
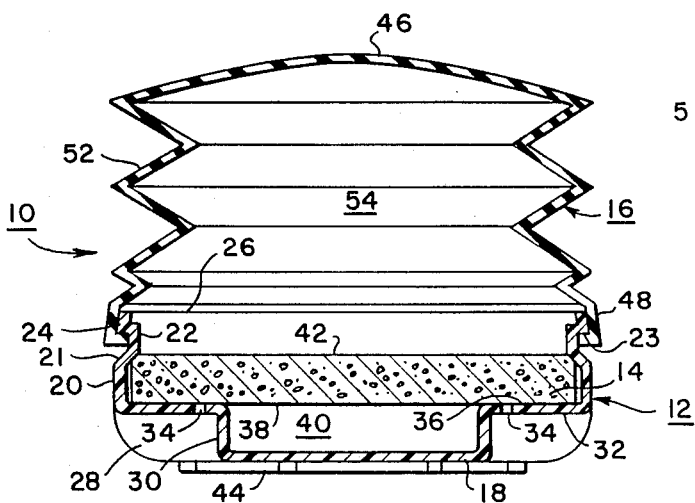
FIG. 5 is an enlarged sectional view as seen substantially from the position 5—5 of FIG. 4.

Base 12, of a relatively rigid molded composition, preferably injection or blow molded, is of an annular generally cup-like configuration including a bottom wall 18 merging with annular sidewall 20 which in turn merges at 21 with an indented sidewall 22 as best seen in FIG. 5. The latter sidewall terminates at a radial offset defining an exterior annular shoulder 23 merging with sidewall 24 that leads to its distal end face 26. Uniformly spaced about the bottom wall are four individual indentations 28 each formed by locally offset walls 30 and 32. Extending through the walls 32 at each of the indentations 28 is at least one breather hole 34 of about 1/16th inch diameter.

The walls 32 overlying each of the indentations 28 collectively cooperate with each other to form an interior shelf plane 36 on which to support the particular fragrance material to be dispensed. In the preferred embodiment disclosed herein, the fragrance material is in the form of a rigid but porous paper base wafer disc 14 previously impregnated with an oil of a selected fragrance, and the disc is secured by the interior angled surface of offset 21. Such wafer discs are of a type available from various commercial sources, and may be in a variety of different fragrances such as lemon, pine, or other desired aromas.

In the relationship shown in FIG. 5, the undersurface 38 of wafer 14 seats on shelf 36 overlying a central cavity portion thereof comprising an interior chamber 40. The upper surface 42 of the wafer in this relation is completely exposed in facing toward the opening at distal end face 26 of the base. For mounting the base onto a recipient support surface, as will be understood, there is provided on the exterior undersurface of wall 18 a peel-away adhesive patch 44 that includes a throwaway tape cover 45.

Bellows 16, preferably of a soft blow molded pliable composition, is of an elongated tubular formation closed at its upper end 46 and open at its bottom as defined by an annular skirt 48. The skirt is adapted to securely mount in a firm clinging grip against sidewall 24 so as to engage and curl under the back shoulder 23 thereat. In this relation, bellows 16, including stepped annular folds 52, defines an internal air chamber 54 confronting the top surface 42 of wafer 14.

Once the individual components are assembled in the foregoing manner, operation of the device represents the height of simplicity. By the mere depression of bellows 16 via a finger 56 of a person wanting to freshen the surrounding air, an air flow is immediately induced through and past the media of wafer 14. In passing through the wafer, the air flow entrains a quantity of the fragrance scent from the wafer 14. As the induced air flow continues, it is emitted as scented air 58 simultaneously through each of the breather holes 34 to the air space surrounding the location of the apparatus 10.

Figure 2:
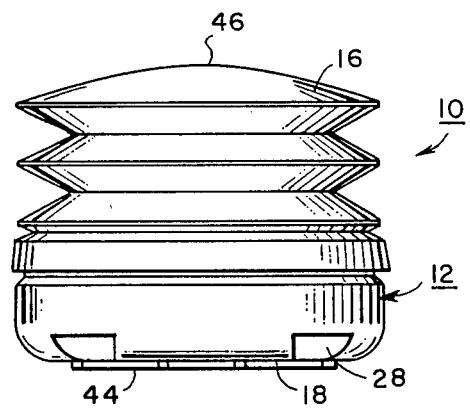
FIG. 2 is a side elevation view of the apparatus in its inoperative condition.
Figure 3:
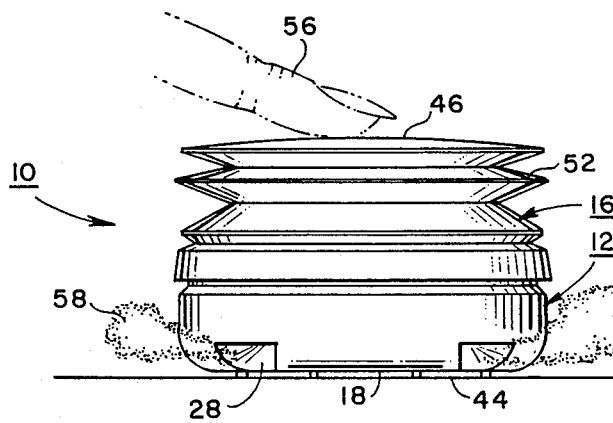
FIG. 3 is a side elevation view of the apparatus in its operative condition.
Figure 4:
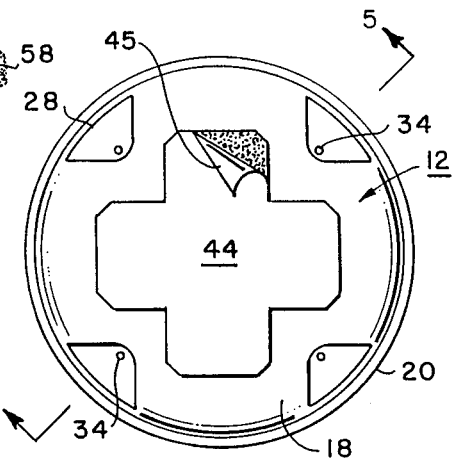
FIG. 4 is an bottom plan view.

Following each scented emission 58, finger 56 is normally removed, immediately enabling resilient reversion of the bellows 16 from its relatively compressed state (illustrated in FIG. 3) to its normal inoperative pre-compressive state (illustrated in FIG. 2). At that point, the bellows can again be compressed for emission of additional scent, which can be easily repeated any number of times until a desired state of air freshening has been achieved. Alternatively, it can be left for use at a later time.

Being that the unit is only operative when compressed, fragrance emission is afforded only on demand and which, via repetitive compressions, can raise the fragrance level of the surrounding air space to any desired level. For large room volumes, it may be desirable to utilize a plurality of individual freshener apparatus 10 at various select locations. Surface mounting of each unit is effected by removing peel-away tape cover 45 and securing the apparatus via pad 44 to a wall, fixture or furniture surface.

As illustrated in FIG. 6, the apparatus 10 can be mounted on the surface of an automobile dashboard 60 at a location in the proximity of steering column 62 and steering wheel 64. Being supported at that location, it is well within reach of the driver who can periodically depress bellows 16 at such time as air freshening is desired. This may prove to be more frequent than otherwise where lingering after-effects of cigarette smoking is prevalent.

In accordance with a unique aspect of the invention, inventive packaging for the merchandising of apparatus 10 is illustrated in FIG. 7 and is designated 66. Comprising the packaging is a rigid base 68, preferably of cardboard, with a mount hole 70 and a cup-like blister wrap 72 secured to base 68 in an enclosing relation about apparatus unit 10 hereof. The blister wrap 72 is of a generally pliable composition, and includes an annular radial flange 74 by which it is adhesively secured to the base 68. Interrupting the continuity of the bond between flange 74 and base 68 is an aperture 76 defining a throughport communication to the interior of the blister wrap 72.

Being that the blister wrap 72 is pliable, but firm and somewhat resilient, operational testing of the unit 10 prior to purchase can be readily performed by depressing the blister wrap (for example by finger 78 applied against the top surface 80 of the blister wrap). Depressing surface 80 then, in turn, depresses bellows top 46 causing a scented emission from the dispenser 10 and, due to the opening 76 in the package, outward through such aperture 76 to the consumer. By this arrangement therefore, the merchandised packaging readily enables on-site testing by the consumer prior to purchase. Not only can the consumer readily test operability, but he can at the same time try the various fragrances in order to select one of choice.

By the above description there has been disclosed a novel air freshener apparatus and novel merchandise packaging therefor. The apparatus represents a convenient and easily operable means for demand issuance of air freshener fragrance selected from a variety of fragrances marketed therewith. The unit is easily mounted onto a recipient surface by the removal of the peel-away tape 45 to expose the adhesive patch 44 and can be repeatedly operated when needed by a mere finger depression of bellows 16. At such time as the fragrance scent of the wafer 14 has been completely dissipated, the unit can be removed and discarded and then subsequently replaced with another. The virtues thereof should be instantly apparent as compared to similar purpose devices of the prior art. Being small, compact, easily mountable onto the recipient surface of choice, and operable by a mere finger actuation of the bellows, affords enhanced versatility in achieving air freshening for a variety of different air spaces that were previously freshened only with comparative difficulty.

Since many changes could be made in the above construction, and many apparently widely different embodiments of this invention could be made without departing from the scope thereof, it is intended that all matter contained in the drawings and specification shall be interpreted as illustrative and not in a limiting sense.

What is claimed is:

1. Air freshener apparatus, comprising:
   a shallow cup-like base of substantially rigid composition having a circumferentially enclosing upstanding wall and futhermore having a plurality of spaced-apart openings disposed about and through said base;
   resilient bellows means disposed above, and coupled with, said base to define an internal air chamber;
   fragrance emitting means; and
   shelf means extending from said upstanding wall supporting the substantial entirety of said fragrance emitting means above said openings and below said internal air chamber, said openings extending through said shelf means;
   whereby when said bellows is manually compressed, air is caused to flow from said internal air chamber through said fragrance emitting means and thereafter through said spaced-apart openings of said base.

2. Air freshener apparatus in accordance with claim 1 in which said fragrance emitting means extends entirely across said base and abuts said circumferentially enclosing upstanding wall.

3. Air freshener apparatus in accordance with claim 2 in which said shelf means comprises an integral support shelf extending radially inward from the enclosing upstanding wall.

4. Air freshener apparatus in accordance with claim 3 in which the upstanding wall of said base is inwardly canted about said fragrance emitting means for securing said fragrance emitting means in position on said support shelf.

5. Air freshener apparatus in accordance with claim 3 in which said support shelf is comprised of a plurality of arcuately spaced ledges integrally joined to the upstanding wall.

6. Air freshener apparatus in accordance with claim 5 including a plurality of indentations formed from the exterior inward in the undersurface of said base for defining the ledges of said support shelf and said openings are disposed through said indentations.

7. Air freshener apparatus in accordance with claim 1 in which said bellows is comprised of a soft pliable composition.

8. Air freshener apparatus in accordance with claim 1 in which said fragrance emitting means comprises a porous paper base impregnated with oils of the fragrance.

9. Air freshener apparatus in accordance with claim 1 including attachment means on said base for mounting the apparatus onto a surface at which it is to be secured.

10. Air freshener apparatus in accordance with claim 9 in which said attachment means comprises an adhesive pad disposed on the underside of said base for said bellows to extend laterally from the plane of a surface to which the apparatus is to be secured.

11. A merchandising package comprising, in combination
   a depressibly actuated aroma dispenser comprising a compressible bellow means which, when depressed, causes an aroma to be emitted from said dispenser; and
   a pliable depressible enclosure surrounding said depressibly actuated aroma dispenser, the top of said enclosure being disposed adjacent the top of said depressibly actuated aroma dispenser;
   said depressible enclosure having an opening disposed near the area of aroma emission from said aroma dispenser;
   whereby the depression of the top of said depressible enclosure consequently causes the depression of the bellows of said depressibly actuated aroma dispenser, thereby to cause the aroma which is being emitted from said dispenser to exit said aperture.

* * * * *